US012064594B2

(12) United States Patent
Rabolli (10) Patent No.: US 12,064,594 B2
(45) Date of Patent: *Aug. 20, 2024

(54) PORT INTERFACE FOR DRUG DELIVERY DEVICE (71) Applicant: Becton, Dickinson and Company, Franklin Lakes, NJ (US)

(72) Inventor: Christina Rabolli, Mahwah, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 17/843,133

(22) Filed: Jun. 17, 2022

(65) Prior Publication Data
US 2022/0323679 A1 Oct. 13, 2022

Related U.S. Application Data (63) Continuation of application No. 16/238,034, filed on Jan. 2, 2019, now Pat. No. 11,364,344.

(60) Provisional application No. 62/612,838, filed on Jan. 2, 2018.

(51) Int. Cl.
A61M 5/142 (2006.01)
A61M 5/145 (2006.01)
A61M 5/158 (2006.01)
A61M 5/20 (2006.01)
A61M 5/24 (2006.01)
A61M 5/31 (2006.01)
A61M 5/315 (2006.01)
(Continued)

(52) U.S. Cl.
CPC .......... *A61M 5/14248* (2013.01); *A61M 5/20* (2013.01); *A61M 5/24* (2013.01); *A61M 5/3146* (2013.01); *A61M 5/31551* (2013.01); *A61M 5/14244* (2013.01); *A61M 5/1452* (2013.01); *A61M 2005/1587* (2013.01); *A61M 5/31541* (2013.01); *A61M 5/31585* (2013.01); *A61M 5/425* (2013.01); *A61M 5/427* (2013.01); *A61M 39/0208* (2013.01); *A61M 2039/0238* (2013.01)

(58) Field of Classification Search
CPC ...... A61M 5/24; A61M 5/14248; A61M 5/20; A61M 5/3146; A61M 5/31551; A61M 5/14244; A61M 5/1452; A61M 5/31541; A61M 5/31585; A61M 5/425; A61M 5/427; A61M 39/0208; A61M 2005/1587; A61M 2039/0238
See application file for complete search history.

(56) References Cited

U.S. PATENT DOCUMENTS 5,620,419 A 4/1997 Lui et al.
7,794,451 B1* 9/2010 Chuter .............. A61M 39/0208
604/93.01

(Continued)

*Primary Examiner* — James D Ponton
(74) *Attorney, Agent, or Firm* — The Webb Law Firm (57) ABSTRACT A drug delivery device includes a housing, a cartridge received within the housing, with the cartridge configured to receive a medicament, a drive assembly received within the housing and configured to engage the cartridge and dispense medicament from the cartridge, and a needle actuator assembly received within the housing, with the needle actuator assembly including a patient needle configured to pierce a patient's skin. A bottom surface of the housing defines a port interface configured to receive an implanted injection port.

8 Claims, 14 Drawing Sheets (51) Int. Cl.
    *A61M 5/42*     (2006.01)
    *A61M 39/02*     (2006.01)

(56) References Cited

U.S. PATENT DOCUMENTS

| | | | |
|---|---|---|---|
| 2002/0123740 A1* | 9/2002 | Flaherty | A61M 5/1452 |
| | | | 604/93.01 |
| 2008/0255516 A1* | 10/2008 | Yodfat | A61M 5/14248 |
| | | | 604/151 |
| 2010/0057010 A1 | 3/2010 | Göransson | |
| 2015/0250944 A1 | 9/2015 | Howell et al. | |
| 2016/0051808 A1 | 2/2016 | Pamment | |
| 2017/0224973 A1 | 8/2017 | Patisteas et al. | |
| 2017/0354788 A1 | 12/2017 | Quinn et al. | |

\* cited by examiner

PORT INTERFACE FOR DRUG DELIVERY DEVICE

CROSS-REFERENCE TO RELATED APPLICATION

The present application is a continuation of U.S. application Ser. No. 16/238,034 entitled "Port Interface for Drug Delivery Device" filed Jan. 2, 2019, which claims priority to U.S. Provisional Application Ser. No. 62/612,838 entitled "Port Interface for Drug Delivery Device" filed Jan. 2, 2018, the entire disclosures of each of which are hereby incorporated by reference.

BACKGROUND OF THE INVENTION

Field of the Invention

The present disclosure relates generally to a drug delivery device and, in particular, to a priming assembly for a drug delivery device.

Description of Related Art

Various types of automatic injection or drug delivery devices have been developed to allow drug solutions and other liquid therapeutic preparations to be administered by untrained personnel or to be self-injected. Generally, these devices include a reservoir that is pre-filled with the liquid therapeutic preparation, and some type of automatic needle-injection mechanism that can be triggered by the user. When the volume of fluid or drug to be administered is generally below a certain volume, such as 1 mL, an auto-injector is typically used, which typically has an injection time of about 10 to 15 seconds. When the volume of fluid or drug to be administered is above 1 mL, the injection time generally becomes longer resulting in difficulties for the patient to maintain contact between the device and the target area of the patient's skin. Further, as the volume of drug to be administered becomes larger, increasing the time period for injection becomes desirable. The traditional method for a drug to be injected slowly into a patient is to initiate an IV and inject the drug into the patient's body slowly. Such a procedure is typically performed in a hospital or outpatient setting.

Certain devices allow for self-injection in a home setting and are capable of gradually injecting a liquid therapeutic preparation into the skin of a patient. In some cases, these devices are small enough (both in height and in overall size) to allow them to be "worn" by a patient while the liquid therapeutic preparation is being infused into the patient. These devices typically include a pump or other type of discharge mechanism to force the liquid therapeutic preparation to flow out of a reservoir and into the injection needle. Such devices also typically include a valve or flow control mechanism to cause the liquid therapeutic preparation to begin to flow at the proper time and a triggering mechanism to initiate the injection.

Figure 16:
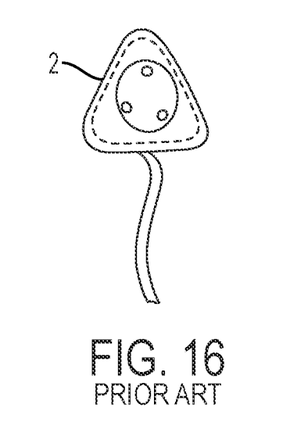
FIG. 16 is top view of a conventional triangular injection port.
Figure 17:
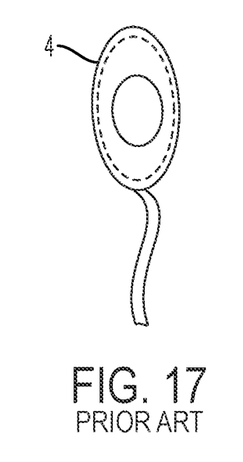
FIG. 17 is top view of a conventional oval injection port.
Figure 18:
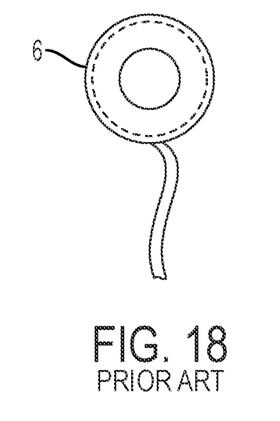
FIG. 18 is top view of a conventional circular injection port.
Figure 19:
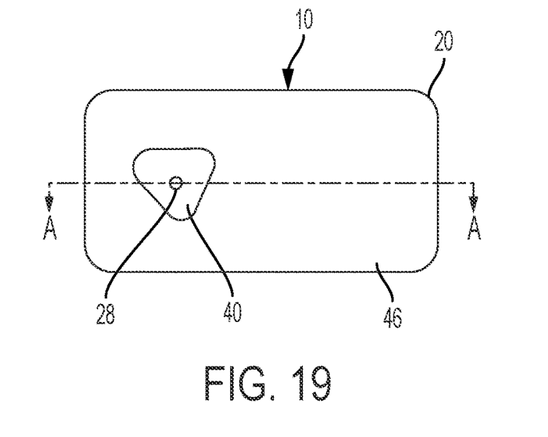
FIG. 19 is a bottom view of a drug delivery device according to one aspect of the present invention.
Figure 20:
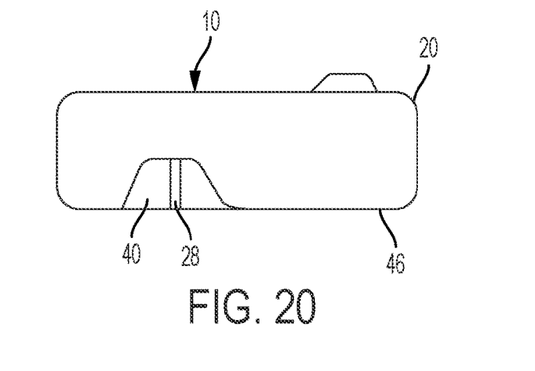
FIG. 20 is a cross-sectional view taken along line A-A shown in FIG. 19.
Figure 21:
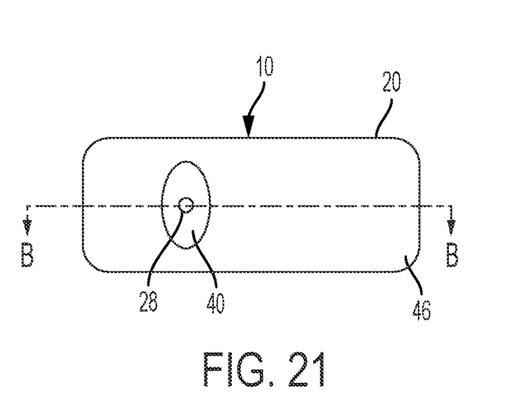
FIG. 21 is a bottom view of a drug delivery device according to one aspect of the present invention.
Figure 22:
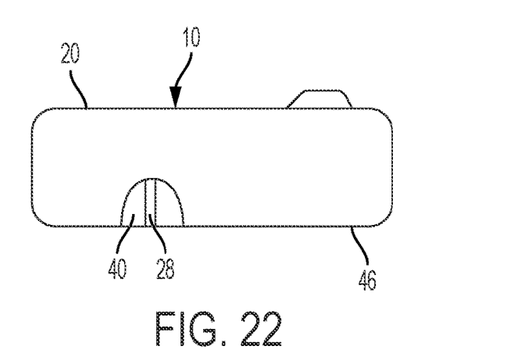
FIG. 22 is a cross-sectional view taken along line B-B shown in FIG. 21.
Figure 23:
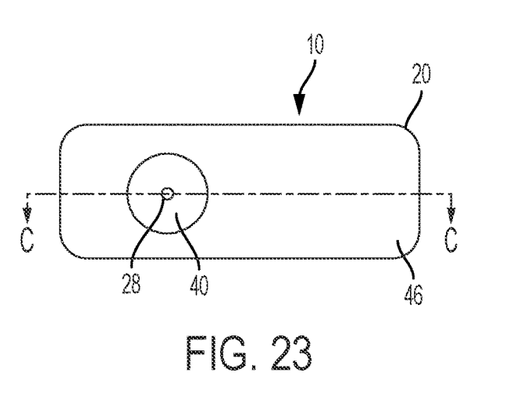
FIG. 23 is a bottom view of a drug delivery device according to one aspect of the present invention.
Figure 24:
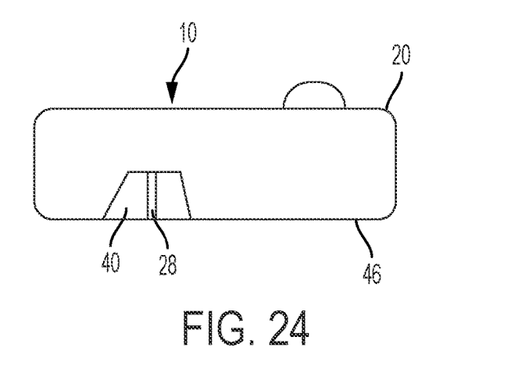
FIG. 24 is a cross-sectional view taken along line C-C shown in FIG. 23.

In treating certain chronic illnesses, such as cancer requiring chemotherapy, an implanted port is inserted under the skin the patient. The port is covered by the skin of the patient. One end of the port has a rubber septum facing the skin surface via which a delivery needle is inserted. The other end of the port is a catheter that is inserted into a vein for intravenous delivery of medicament. Typically, an infusion set with a needle is used to deliver medicament through the port, which is usually accomplished in a clinical setting by a heath care provider. Conventional ports 2, 4, 6 are shown in FIGS. 16-18 and include a triangular port 2 (FIG. 16), an oval port 4 (FIG. 17), and a round port 6 (FIG. 18), although other shaped ports may be utilized.

SUMMARY OF THE INVENTION

In one aspect, a drug delivery device includes a housing, a cartridge received within the housing, with the cartridge configured to receive a medicament, a drive assembly received within the housing and configured to engage the cartridge and dispense medicament from the cartridge, and a needle actuator assembly received within the housing, with the needle actuator assembly comprising a patient needle configured to pierce a patient's skin. A bottom surface of the housing defining a port interface configured to receive an implanted injection port.

The port interface may be a recess having a shape corresponding to a shape of an implanted injection port. The shape of the recess may be one of triangular, oval, and circular.

The housing may include a main body and an interface plate secured to the main body, with the interface plate defining the bottom surface of the housing. The interface plate may be detachably secured to the main body via a connection arrangement. The connection arrangement may include corresponding snap members provided on the main body of the housing and the interface plate. The interface plate may include an opening having a shape corresponding to a shape of an implanted injection port.

In a further aspect, a port interface plate for a drug delivery device including a housing, a cartridge received within the housing, a drive assembly received within the housing and configured to engage the cartridge and dispense medicament from the cartridge, and a needle actuator assembly received within the housing, includes a plate body having a first side and a second side positioned opposite from the first side, and a port interface configured to receive an implanted injection port.

The port interface may be an opening having a shape corresponding to a shape of an implanted injection port. The shape of the opening may be one of triangular, oval, and circular. The port interface plate may include a connection arrangement configured to secure the port interface plate to the housing the drug delivery device. The connection arrangement may include snap members provided on the plate body of the interface plate.

In a further aspect, a drug delivery device includes a housing including a bottom surface defining a port recess, a cartridge received within the housing, with the cartridge configured to receive a medicament, a drive assembly received within the housing and configured to engage the cartridge and dispense medicament from the cartridge, a needle actuator assembly received within the housing, with the needle actuator assembly comprising a patient needle configured to pierce a patient's skin, and a port interface plate configured to be secured to the bottom surface of the housing. The port interface plate includes a port interface configured to be aligned with the port recess of the housing when the port interface plate is secured to the housing.

The port interface plate may include a connection arrangement configured to secure the port interface plate to the housing the drug delivery device.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

DETAILED DESCRIPTION

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Referring to FIGS. 1-15, a drug delivery device 10 according to one aspect of the present disclosure includes a drive assembly 12, a container 14, a valve assembly 16, and a needle actuator assembly 18. The drive assembly 12, the container 14, the valve assembly 16, and the needle actuator assembly 18 are at least partially positioned within a cavity defined by a housing 20. The housing 20 includes a top portion 22 and a bottom portion 24, although other suitable arrangements for the housing 20 may be utilized. In one aspect, the drug delivery device 10 is an injector device configured to be worn or secured to a user and to deliver a predetermined dose of a medicament provided within the container 14 via injection into the user. The device 10 may be utilized to deliver a "bolus injection" where a medicament is delivered within a set time period. The medicament may be delivered over a time period of up to 45 minutes, although other suitable injection amounts and durations may be utilized. A bolus administration or delivery can be carried out with rate controlling or have no specific rate controlling. The device 10 may deliver the medicament at a fixed pressure to the user with the rate being variable. The general operation of the device 10 is described below in reference to FIGS. 1-15.

Referring again to FIGS. 1-15, the device 10 is configured to operate through the engagement of an actuation button 26 by a user, which results in a needle 28 of the needle assembly 18 piercing the skin of a user, the actuation of the drive assembly 12 to place the needle 28 in fluid communication with the container 14 and to expel fluid or medicament from the container 14, and the withdrawal of the needle 28 after injection of the medicament is complete. The general operation of a drug delivery system is shown and described in International Publication Nos. 2013/155153 and 2014/179774, which are hereby incorporated by reference in their entirety. The housing 20 of the device 10 includes an indicator window 30 for viewing an indicator arrangement 32 configured to provide an indication to a user on the status of the device 10 and a container window 31 for viewing the container 14. The indicator window 30 may be a magnifying lens for providing a clear view of the indicator arrangement 32. The indicator arrangement 32 moves along with the needle actuator assembly 18 during use of the device 10 to indicate a pre-use status, use status, and post-use status of the device 10. The indicator arrangement 32 provides visual indicia regarding the status, although other suitable indicia, such an auditory or tactile, may be provided as an alternative or additional indicia.

Figure 1:
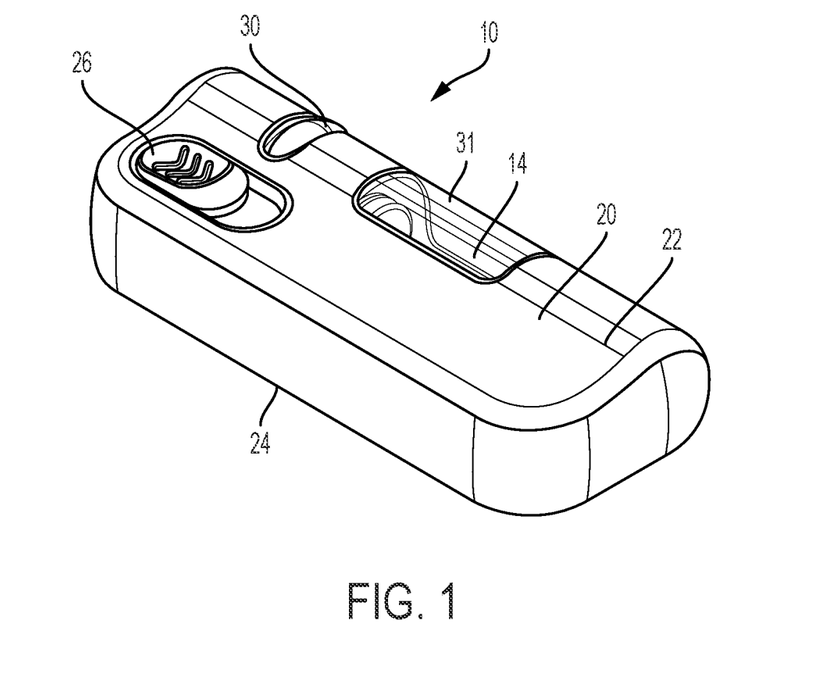
FIG. 1 is a perspective view of a drug delivery system according to one aspect of the present invention.
Figure 2:
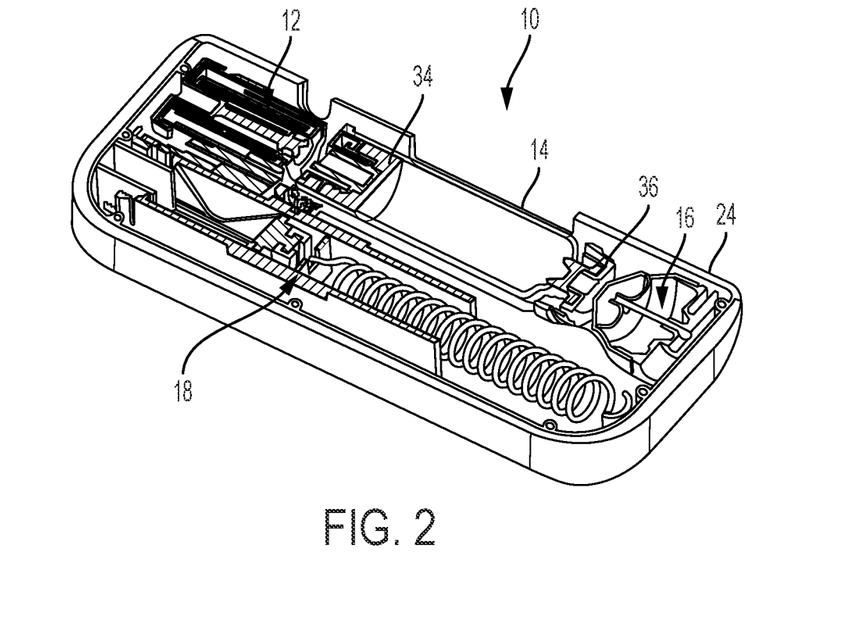
FIG. 2 is a perspective, cross-sectional view of the drug delivery system of FIG. 1 according to one aspect of the present invention.
Figure 3:
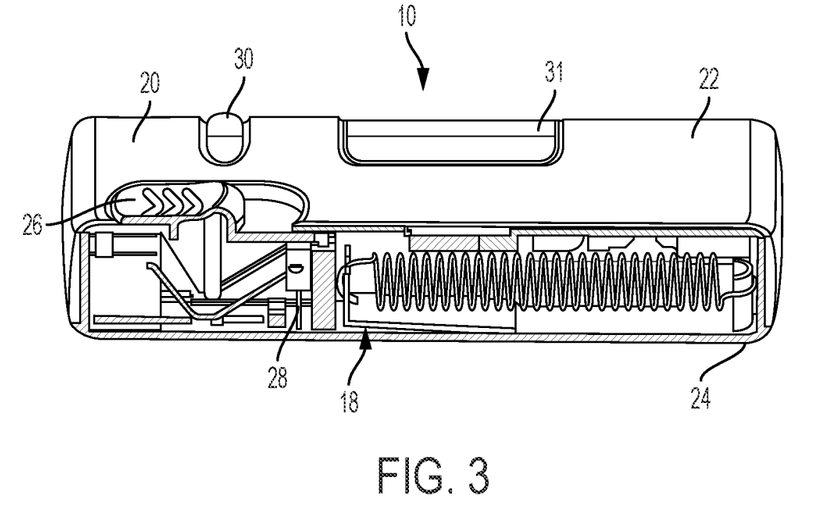
FIG. 3 is a front, cross-sectional view of the drug delivery system of FIG. 1 according to one aspect of the present invention.
Figure 4:
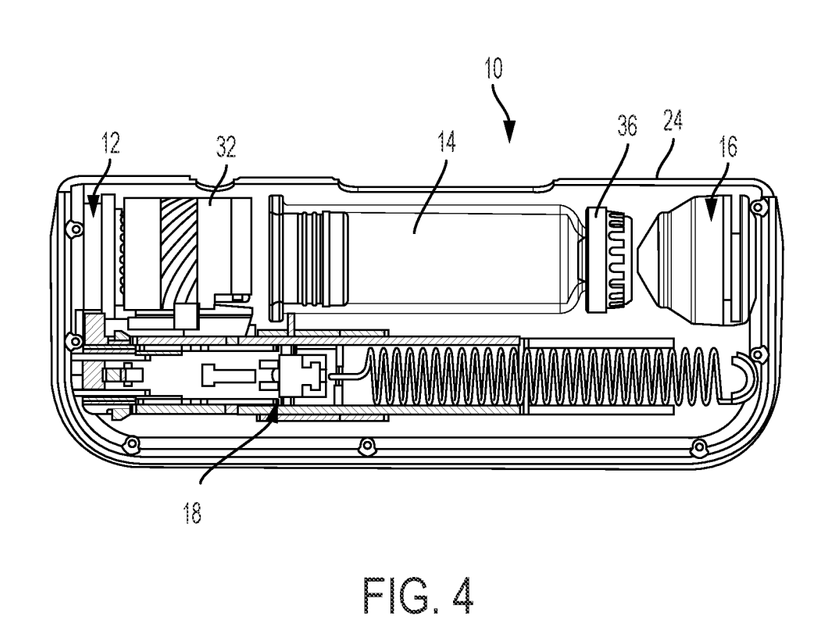
FIG. 4 is a top view of the drug delivery system of FIG. 1 according to one aspect of the present invention, showing a top portion of the housing removed and the drug delivery system in a pre-use position.
Figure 5:
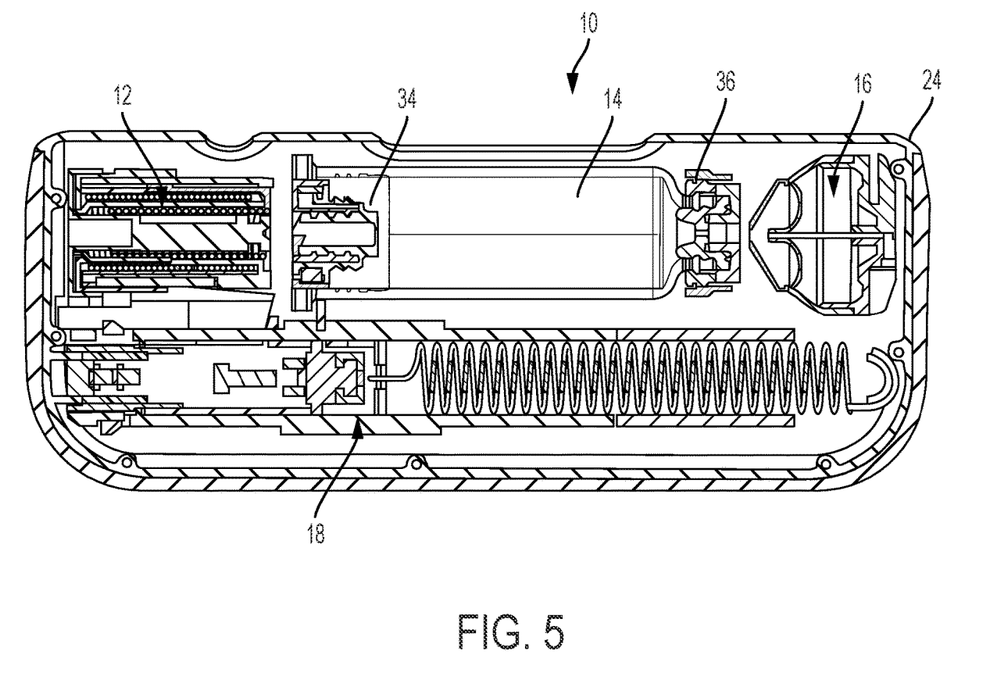
FIG. 5 is a top, cross-sectional view of the drug delivery system of FIG. 1 according to one aspect of the present invention, showing the drug delivery system in a pre-use position.
Figure 6:
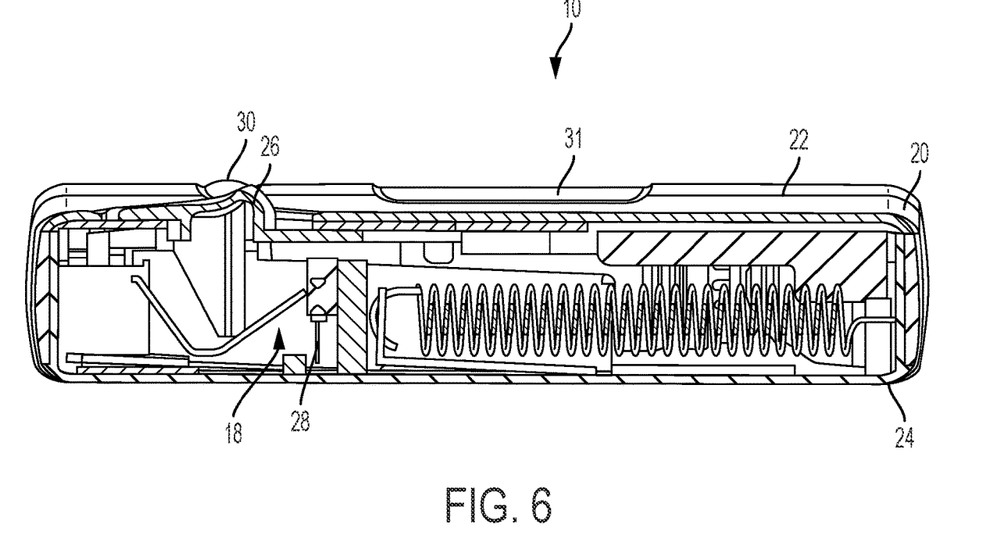
FIG. 6 is a front, cross-sectional view of the drug delivery system of FIG. 1 according to one aspect of the present invention, showing the drug delivery system in a pre-use position.
Figure 7:
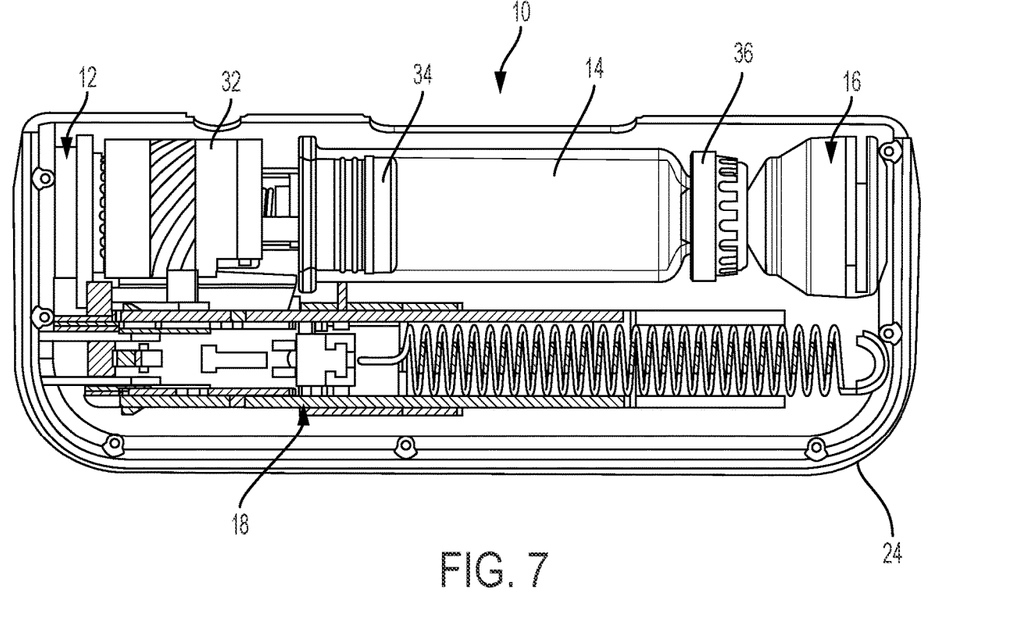
FIG. 7 is a top view of the drug delivery system of FIG. 1 according to one aspect of the present invention, showing a top portion of the housing removed and the drug delivery system in an initial actuation position.
Figure 8:
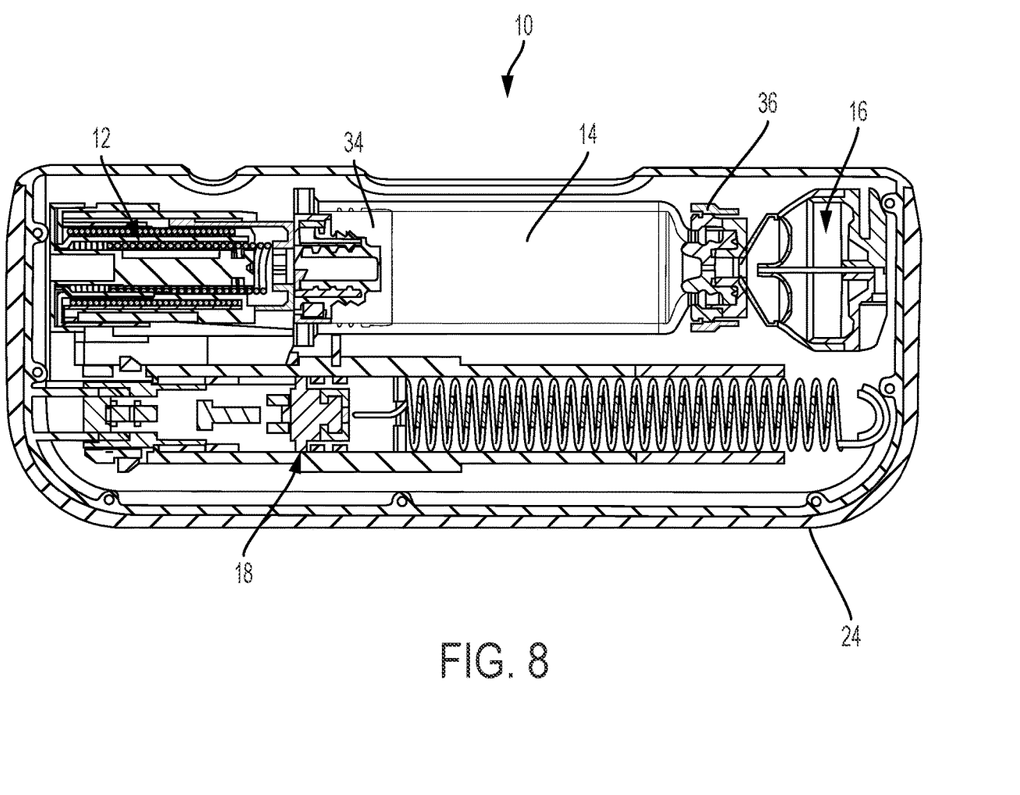
FIG. 8 is a top, cross-sectional view of the drug delivery system of FIG. 1 according to one aspect of the present invention, showing the drug delivery system in an initial actuation position.
Figure 9:
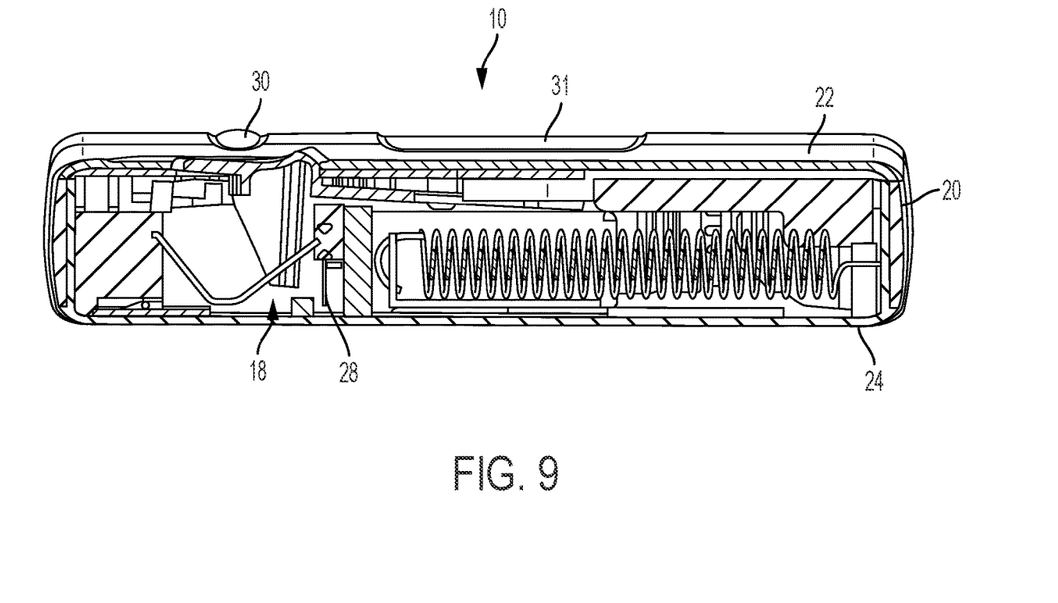
FIG. 9 is a front, cross-sectional view of the drug delivery system of FIG. 1 according to one aspect of the present invention, showing the drug delivery system in an initial actuation position.

Referring to FIGS. 4-6, during a pre-use position of the device 10, the container 14 is spaced from the drive assembly 12 and the valve assembly 16 and the needle 28 is in a retracted position. During the initial actuation of the device 10, as shown in FIGS. 7-9, the drive assembly 12 engages the container 14 to move the container 14 toward the valve assembly 16, which is configured to pierce a closure 36 of the container 14 and place the medicament within the container 14 in fluid communication with the needle 28 via a tube (not shown) or other suitable arrangement. The drive assembly 12 is configured to engage a stopper 34 of the container 14, which will initially move the entire container 14 into engagement with the valve assembly 16 due to the incompressibility of the fluid or medicament within the container 14. The initial actuation of the device 10 is caused by engagement of the actuation button 26 by a user, which releases the needle actuator assembly 18 and the drive assembly 12 as discussed below in more detail. During the initial actuation, the needle 28 is still in the retracted position and about to move to the extended position to inject the user of the device 10.

Figure 10:
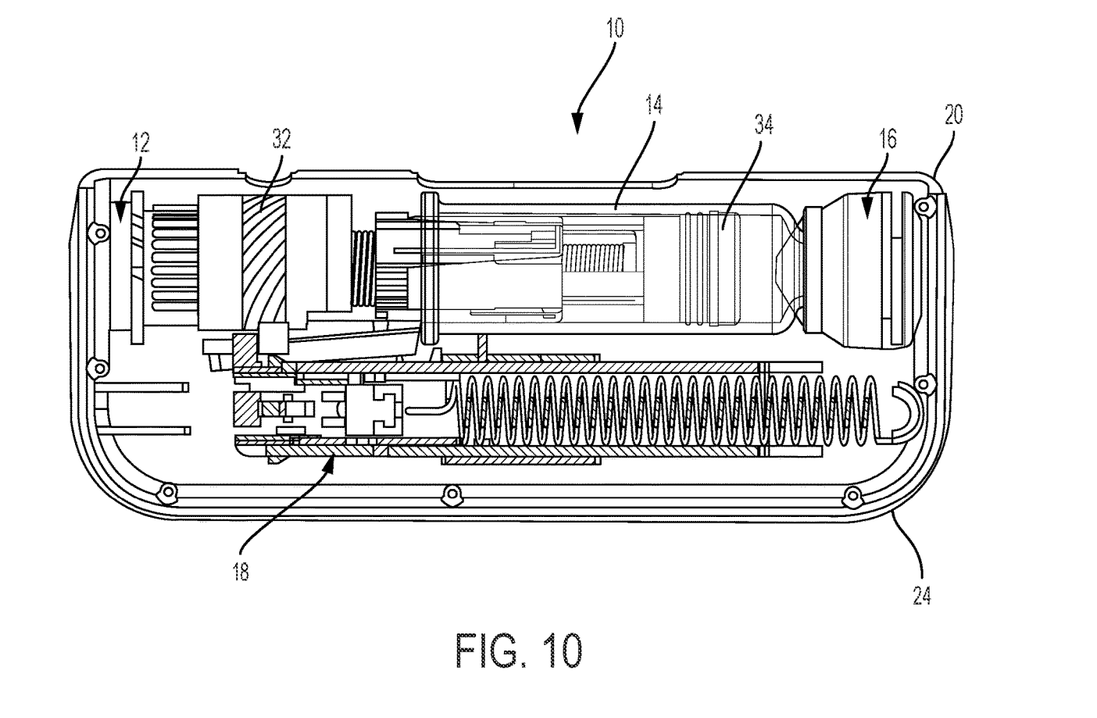
FIG. 10 is a top view of the drug delivery system of FIG. 1 according to one aspect of the present invention, showing a top portion of the housing removed and the drug delivery system in a use position.
Figure 11:
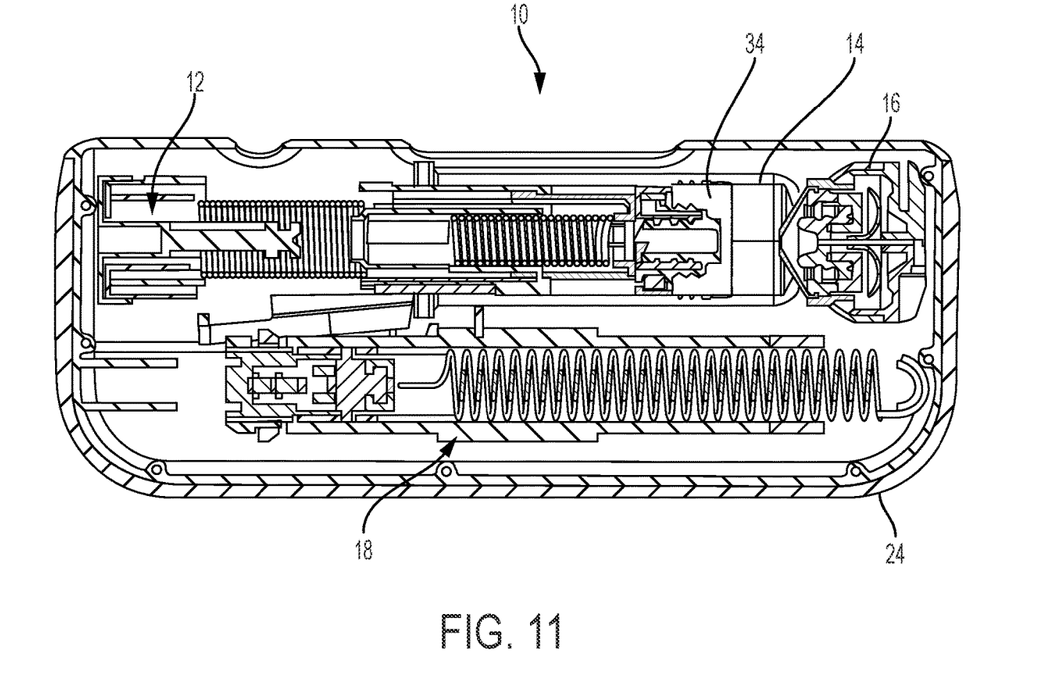
FIG. 11 is a top, cross-sectional view of the drug delivery system of FIG. 1 according to one aspect of the present invention, showing the drug delivery system in a use position.
Figure 12:
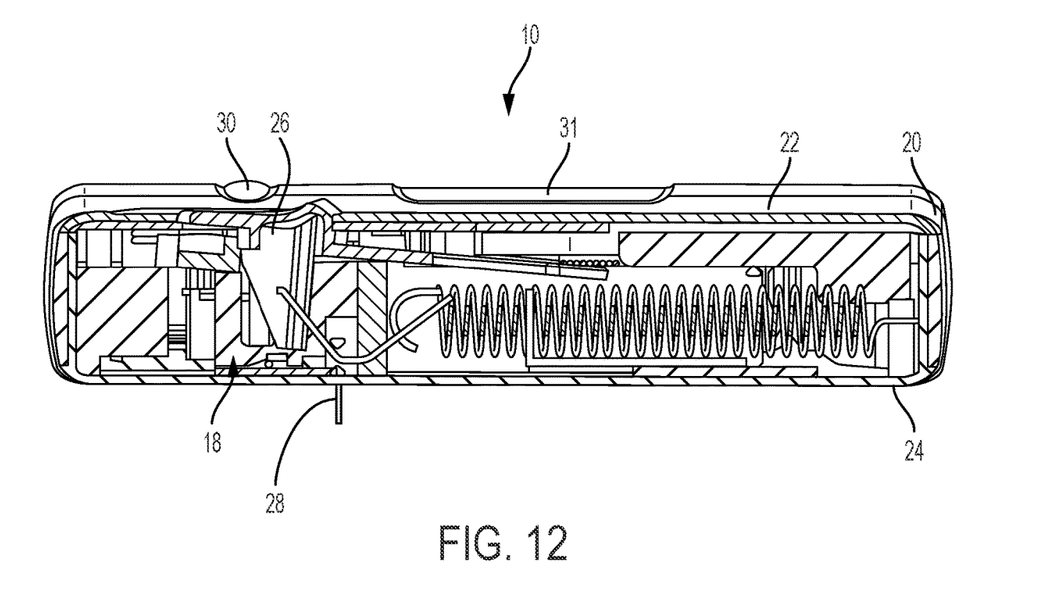
FIG. 12 is a front, cross-sectional view of the drug delivery system of FIG. 1 according to one aspect of the present invention, showing the drug delivery system in a use position.
Figure 13:
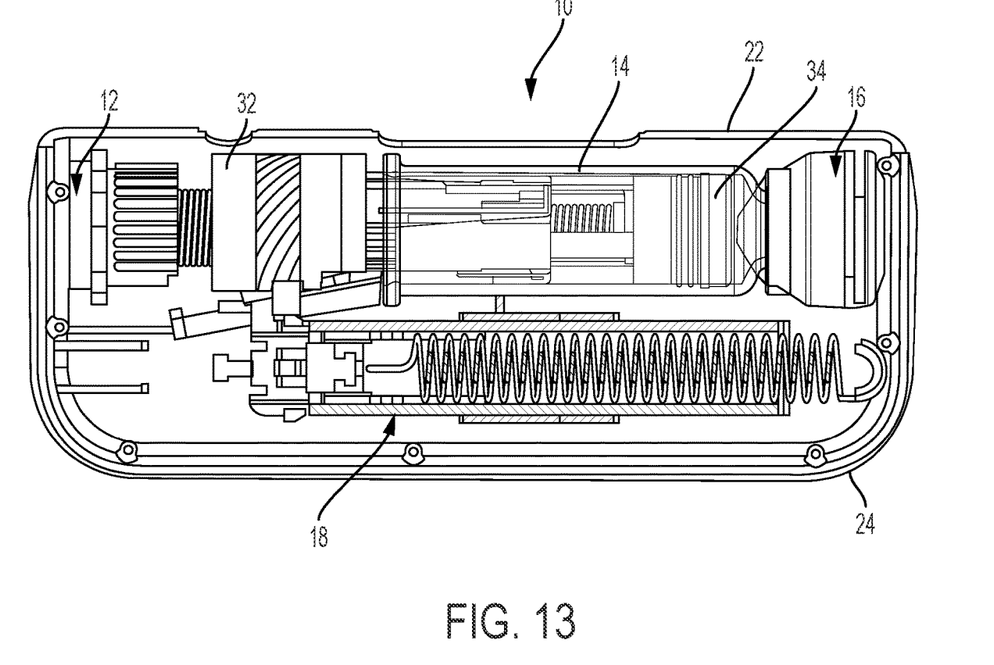
FIG. 13 is a top view of the drug delivery system of FIG. 1 according to one aspect of the present invention, showing a top portion of the housing removed and the drug delivery system in a post-use position.
Figure 14:
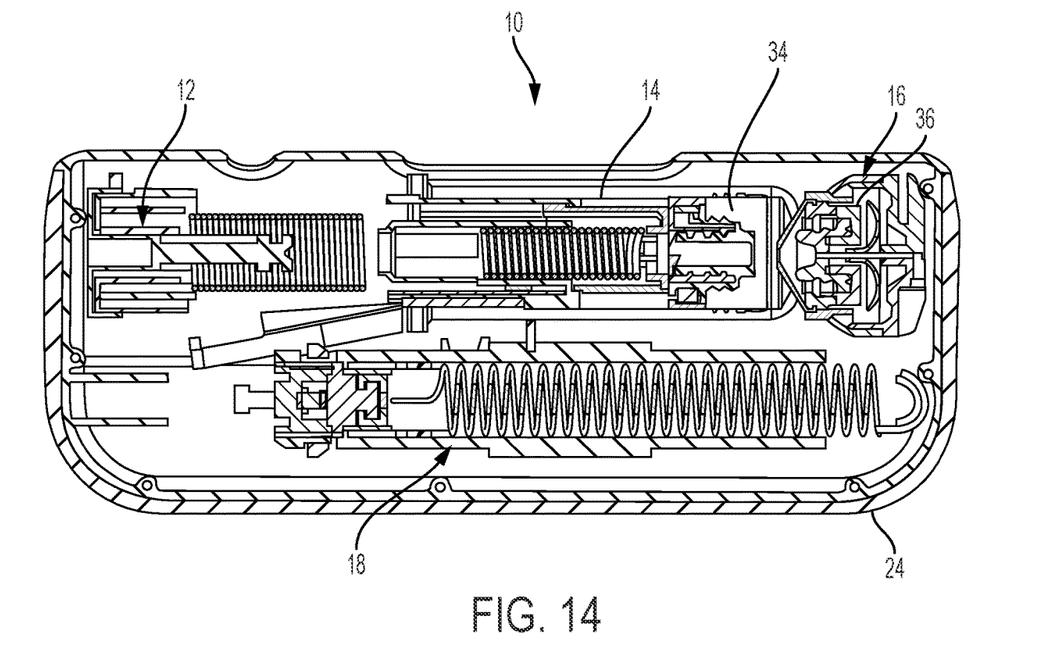
FIG. 14 is a top, cross-sectional view of the drug delivery system of FIG. 1 according to one aspect of the present invention, showing the drug delivery system in a post-use position.
Figure 15:
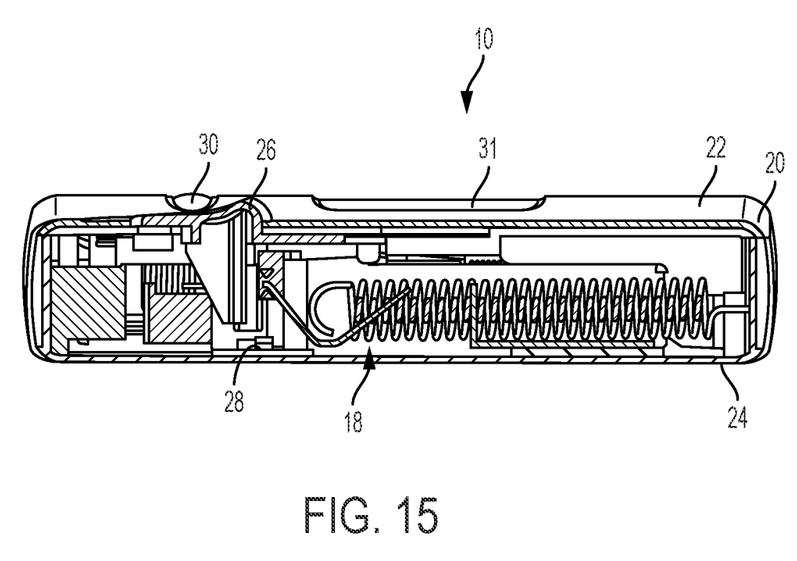
FIG. 15 is a front, cross-sectional view of the drug delivery system of FIG. 1 according to one aspect of the present invention, showing the drug delivery system in a post-use position.

During the use position of the device 10, as shown in FIGS. 10-12, the needle 28 is in the extended position at least partially outside of the housing 20 with the drive assembly 12 moving the stopper 34 within the container 14 to deliver the medicament from the container 14, through the needle 28, and to the user. In the use position, the valve assembly 16 has already pierced a closure 36 of the container 14 to place the container 14 in fluid communication with the needle 28, which also allows the drive assembly 12 to move the stopper 34 relative to the container 14 since fluid is able to be dispensed from the container 14. At the post-use position of the device 10, shown in FIGS. 13-15, the needle 28 is in the retracted position and engaged with a pad 38 to seal the needle 28 and prevent any residual flow of fluid or medicament from the container 14. The container 14 and valve assembly 16 may be the container 14 and valve assembly 16 shown and described in International Publication No. WO 2015/081337, which is hereby incorporated by reference in its entirety.

Referring to FIGS. 19-35, a port interface 40 for receiving an implanted injection port 42, such as the ports 2, 4, 6 shown in FIGS. 16-18, is provided. The port interface 40 is configured for receiving the port 2, 4, 6 such that a needle of a drug delivery device, such as the needle 28 of drug delivery device 10, is aligned with a septum 44 of the port. The port interface 40 may be provided with the drug delivery device 10 described above and shown in FIGS. 1-15, although the port interface 40 may be provided on other suitable drug delivery devices.

Referring to FIGS. 19-23, a bottom surface 46 of the housing 20 of the drug delivery device 10 defines the port interface 40. The port interface 40 is a recess having a shape corresponding to a shape of the implanted injection port 2, 4, 6. The shape of the recess may be triangular (FIGS. 19 and 20), oval (FIGS. 21 and 22), or circular (FIGS. 23 and 24), although other suitable shapes may be utilized to receive any other size and shape of port. The port interfaces 40 shown in FIGS. 19-24 are configured to receive the ports 2, 4, 6 shown in FIGS. 16-18, respectively. The size and shape of the recess may be configured to partially or entirely receive a portion of the port 2, 4, 6 that extends from a skin surface 48 of a patient to ensure the needle 28 is aligned with the septum 44 of the port 2, 4, 6. The bottom surface 46 of the housing 20 may include an adhesive material (not shown) to secure the device 10 to the skin surface 48 of the patient, although other suitable arrangements for securing the device 10 to the patient may be utilized.

Figure 25:
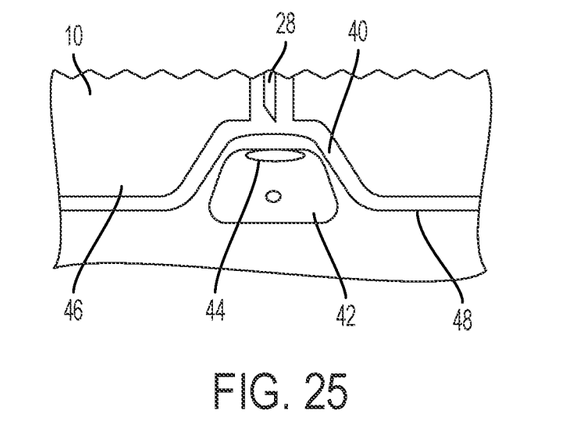
FIG. 25 is a cross-sectional view of a drug delivery device according to one aspect of the present invention, showing a pre-injection position of the device.
Figure 26:
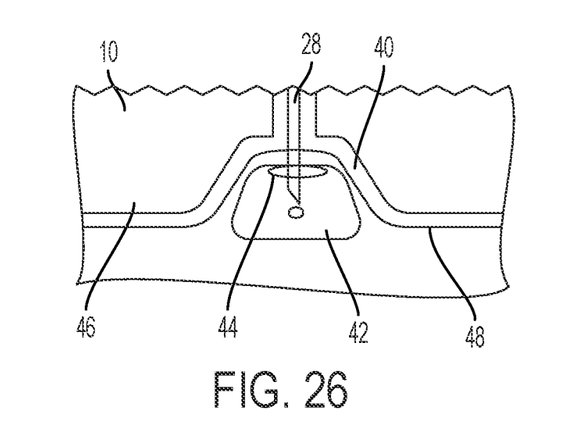
FIG. 26 is a cross-sectional view of a drug delivery device according to one aspect of the present invention, showing an injection position of the device.

Referring to FIGS. 25 and 26, the port interface 40 is aligned with the port 2, 4, 6 and the housing 20 is engaged with the skin surface 48 of the patient. The port interface 40 receives the port 2, 4, 6 such that the needle 28 is aligned with the septum 44 of the port 2, 4, 6. During injection, the needle 28 pierces the septum 44 of the port 2, 4, 6 to deliver medicament from the device 10 to the patient via the port 2, 4, 6.

Referring to FIGS. 27-35, rather than providing the port interface 40 as an integral part of the housing of the device 10, the port interface 40 is provide via a port interface plate 60. The port interface plate 60 is detachably secured to a main body 62 of the housing 20 of the device 10 via a connection arrangement 64. The port interface plate 60 includes a plate body 66 having a first side 68 and a second side 70 positioned opposite the first side 68. The plate body 66 defines the port interface 40. In one aspect, the port interface 40 may be an opening extending from the first side 68 of the plate body 66 to the second side 70 of the plate body 66. The port interface 40 of the port interface plate 60 may be triangular (FIGS. 29 and 30), oval (FIGS. 31 and 32), or circular (FIGS. 33 and 34), although other suitable shapes may be utilized to receive any other size and shape of port. The port interfaces 40 shown in FIGS. 29-34 are configured to receive the ports 2, 4, 6 shown in FIGS. 16-18, respectively. The connection arrangement 64 of the port interface plate 60 may be snap members 72 provided on the plate body, which cooperate with and engage corresponding snap members 74 provided on the main body of the device 10, although any other suitable securing arrangement may be provided.

Figure 27:
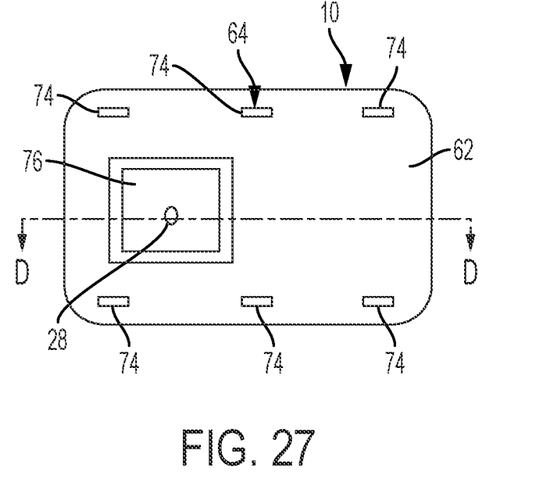
FIG. 27 is a bottom view of a drug delivery device according to one aspect of the present invention.
Figure 28:
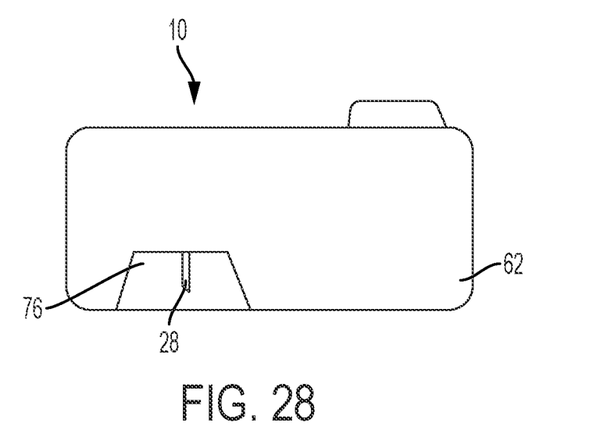
FIG. 28 is a cross-sectional view taken along line D-D shown in FIG. 27.
Figure 29:
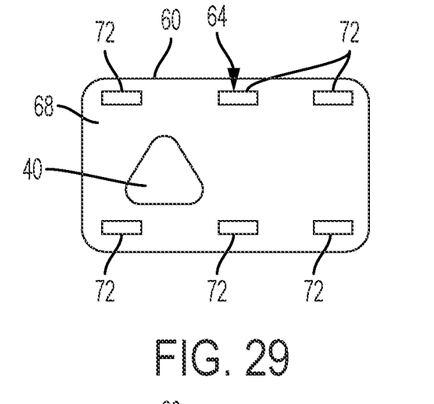
FIG. 29 is a top view of a port interface plate according to one aspect of the present invention.
Figure 30:
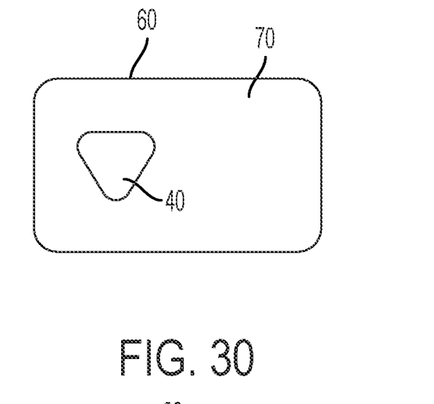
FIG. 30 is a bottom view of the port interface plate of FIG. 29 according to one aspect of the present invention.
Figure 31:
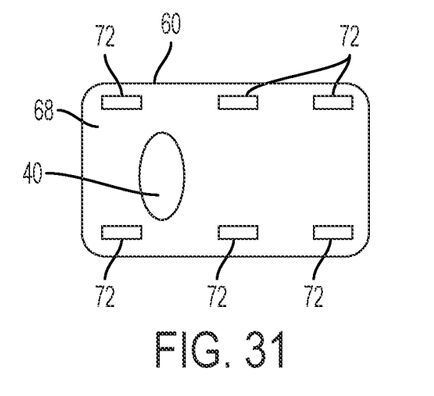
FIG. 31 is a top view of a port interface plate according to one aspect of the present invention.
Figure 32:
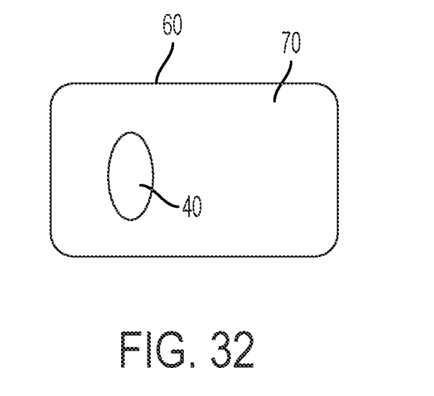
FIG. 32 is a bottom view of the port interface plate of FIG. 31 according to one aspect of the present invention.
Figure 33:
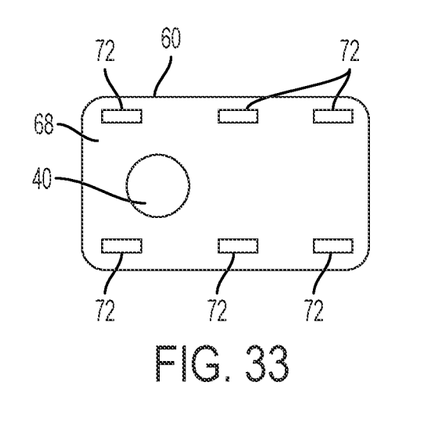
FIG. 33 is a top view of a port interface plate according to one aspect of the present invention.
Figure 34:
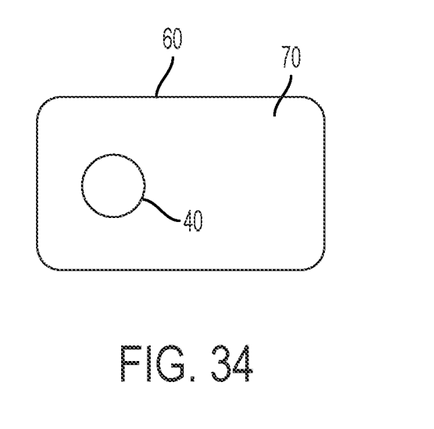
FIG. 34 is a bottom view of the port interface plate of FIG. 33 according to one aspect of the present invention.

Referring to FIG. 27, the main body 62 of the device 10 includes a port recess 76 configured to accommodate any one of the port interfaces 40 shown in FIGS. 29-34. The port interface plate 60 is secured to the main body 62 of the housing 20 such that the port interface 40 is aligned with the port recess 76 of the housing 20. In other words, the port recess 76 of the main body 62 has sufficient clearance to accommodate any port shape. One of the port interface plates 60 may be selected and secured to the main body 62 depending on the size and shape of the implanted injection port 2, 4, 6.

Figure 35:
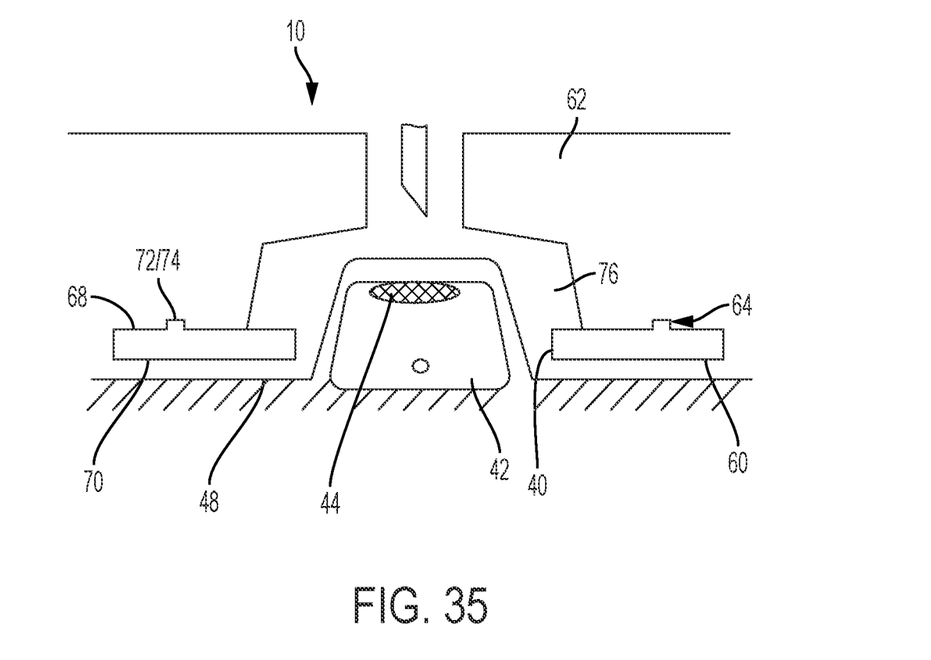
FIG. 35 is a cross-sectional view of a drug delivery device according to one aspect of the present invention, showing a pre-injection position of the device.

Referring to FIG. 35, one of the port interface plates 60 is connected to the main body 62 of the device 10 with the port interface plate 60 secured to the skin surface 48 of the patient. The port interface plate 60 may include an adhesive material (not shown) to secure the plate 60 and device 10 to the skin surface 48 of the patient, although other suitable arrangements for securing the plate 60 and device 10 to the patient may be utilized. The port interface 40 of the plate 60 is aligned with the septum 44 of the port 2, 4, 6. During injection, the needle 28 pierces the septum 44 of the port 2, 4, 6 to deliver medicament from the device 10 to the patient via the port 2, 4, 6.

Elements of one disclosed aspect can be combined with elements of one or more other disclosed aspects to form different combinations, all of which are considered to be within the scope of the present invention.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A drug delivery device comprising:
a housing;
an interface plate engageable with the housing;
a cartridge received within the housing, the cartridge configured to receive a medicament;
a drive assembly received within the housing and configured to engage the cartridge and dispense the medicament from the cartridge; and
a needle actuator assembly received within the housing, the needle actuator assembly comprising a patient needle configured to pierce a patient's skin,
wherein a bottom surface of the housing defines a port recess configured to receive an implanted injection port, and
wherein the interface plate defines an opening configured to receive the implanted injection port, and
wherein the interface plate extends at least partially into the port recess.

2. The device of claim 1, wherein the opening of the interface plate defines a port interface, and wherein the port interface has a shape corresponding to a shape of the implanted injection port.

3. The device of claim 2, wherein the shape of the port recess is one of triangular, oval, and circular.

4. The device of claim 1, wherein the housing comprises a main body and the interface plate is secured to the main body, the interface plate defining a bottom surface of the drug delivery device.

5. The device of claim 4, wherein the interface plate is detachably secured to the main body via a connection arrangement.

6. The device of claim 5, wherein the connection arrangement comprises corresponding snap members provided on the main body of the housing and the interface plate.

7. The device of claim 4, wherein the opening in the interface plate comprises a shape corresponding to a shape of the implanted injection port.

8. The device of claim 7, wherein the shape of the opening is one of triangular, oval, and circular.

* * * * *